United States Patent
Lee

(10) Patent No.: US 6,412,542 B1
(45) Date of Patent: Jul. 2, 2002

(54) CENTRIFUGAL DENTAL CASTING STATION FOR ROTATING CASTING MACHINE

(76) Inventor: Kwang H. Lee, 303 S. Glenoaks Blvd., #14, Burbank, CA (US) 91502

( * ) Notice: Subject to any disclaimer, the term of this patent is extended or adjusted under 35 U.S.C. 154(b) by 0 days.

(21) Appl. No.: 09/545,027

(22) Filed: Apr. 7, 2000

(51) Int. Cl.[7] .......................... B22D 13/12; B29C 33/22
(52) U.S. Cl. ...................................... 164/286; 249/139
(58) Field of Search .................................. 164/286, 287, 164/288, 289, 290, 291, 292, 293, 294, 295, 296, 297, 298, 299, 300, 301; 249/139, 54; 425/425

(56) References Cited

U.S. PATENT DOCUMENTS

| | | | |
|---|---|---|---|
| 2,462,113 A | 2/1949 | Lipson et al. | 425/146 |
| 3,818,974 A | * 6/1974 | Eberle | 164/255 |
| 4,298,019 A | 11/1981 | Daransky et al. | 137/9 |
| 4,752,203 A | * 6/1988 | Kanzaki | 425/182 |
| 5,409,585 A | 4/1995 | Essary et al. | 204/180.7 |
| 5,678,734 A | 10/1997 | Walker | 222/146.5 |

* cited by examiner

*Primary Examiner*—M. Alexandra Elve
*Assistant Examiner*—Len Tran
(74) *Attorney, Agent, or Firm*—John K. Park; Park & Sutton LLP

(57) ABSTRACT

A centrifugal dental casting station for a rotating casting machine comprises a tank having a base, side walls, a ceiling having first slide holes, a first opening, a closing member for the first opening, and a cross-traversing partition attached to the base and the side walls in the tank. The base, the side walls and the ceiling form a cavity, and the cavity can be filled with a filler material through the first opening. A support member is attached to the tank for supporting the rotating casting machine thereon. The casting station provides a substantially stable platform for operating the rotating casting machine thereon.

17 Claims, 4 Drawing Sheets

CENTRIFUGAL DENTAL CASTING STATION FOR ROTATING CASTING MACHINE

BACKGROUND OF THE INVENTION

The present invention relates to a casting station. More particularly, the present invention relates to a centrifugal dental casting station for a rotating casting machine which significantly improves usability.

A centrifugal casting machine uses an inertial momentum of rotation to inject a dissolved metal into a target mold. So there is required a weighty casting station that can absorb the rotational vibration.

Most conventional casting stations on the market such as induction casting units are provided together with casting machines. Accordingly the induction casting units are priced so high that more than 80% of dental laboratories in America choose centrifugal casting machines. The casting station applicable to the centrifugal casting machine has limitation in development and distribution due primarily to its weight.

When using a centrifugal casting machine, a variety of substitutes are selected for absorbing its vibration. For example, a wooden box or an oil drum may be filled with concrete and the centrifugal casting machine is placed thereon. However, the thusly installed casting station is discarded when moving the dental lab, because the concrete structure is permanent and unwieldly heavy to transport and a new casting station becomes improvised on the spot, thereby wasting money and time.

Further, such an improvised casting station may deteriorate casting quality and durability of the casting machine, and accordingly unbalanced level of the casting machine may further increase noise and vibration. Accordingly, there is a need for a casting station to efficiently support the centrifugal casting machine thereon and effectively absorb the vibration of the casting machine.

SUMMARY OF THE INVENTION

The present invention is contrived to overcome the conventional disadvantages. Therefore, it is an object of the present invention to provide a centrifugal dental casting station for a rotation casting machine which improves usability and workability.

To achieve the above-described object, the centrifugal dental casting station comprises a tank and a support means attached to the tank. The support means supports the rotating casting machine thereon so that the casting station can provide a substantially stable platform for operating the rotating casting machine thereon.

The tank comprises a base, side walls, a ceiling, a first opening, a closing means for the first opening, and a cross-traversing partition attached to the base and the side walls therein. The side walls may have middle portions and the ceiling may be attached to about the middle portions of the side walls.

The cross-traversing partition has an upper edge thereon. The base, the side walls and the ceiling form a cavity. The cavity can be filled with a filler material through the first opening. The closing means may be a cap covering the first opening to enclose the filler material when the filler material is inserted into the cavity.

In an embodiment, the support means may be a plurality of bolts. The bolts provide attachment of the rotating casting machine to the ceiling. The support means may further comprise at least one bolt mount fixedly attached to the upper edge of the cross-traversing partition and having a plurality of slide holes therethrough. The bolts are engaged through the slide holes to the casting machine so that the slide holes enable a slidably adjustable bolt engagement depending upon the rotating casting machine.

For a better performance, the casting station further comprises a protective wall mounted on the tank. The protective wall includes an inner protector. The inner protector together with the protective wall provides a substantial protection for the user when the rotating casting machine is installed onto the casting station.

The tank further comprises a second opening for draining the filler material out of the tank, a valve for regulating an outflow of the filler material through the second opening, and baffles attached to the base and the side walls inside the tank. The baffles serve to minimize the thickness and maximize the strength of the side walls. Also, the cross-traversing partition together with the upper edge reliably supports the bolts being engaged to the casting machine.

The advantages of the present invention are numerous. First, the present invention replaces the currently improvised casting stations for centrifugal dental casting machines being used in more than 80% dental labs in America and provides a standardized centrifugal dental casting station for thereby improving usability and work performance.

Second, the overall weight of the casting station is substantially decreased by thinnerizing the side walls while improving strength with the baffle and cross-traversing partition attachment to the side walls. Third, the filler material in the tank can be easily adjusted in amount depending upon requirements in view of noise and vibration generated by the casting machine, thereby improving stability.

Most importantly, the casting station according to the present invention, because of its lightweight and the adjustability of its weight, enables an easy installation and an easy transportation. Moreover, also because of its lightweight, when the filler material is removed, the centrifugal dental casting station along with the rotating casting machine can be easily leveled and its level can be easily adjusted when required in the future.

BRIEF DESCRIPTION OF THE DRAWINGS

These and other features, aspects, and advantages of the present invention will become better understood with regard to the following description, appended claims, and accompanying drawings which illustrate examples of the invention, wherein:

DETAILED DESCRIPTION OF THE PREFERRED EMBODIMENTS

Figure 1:
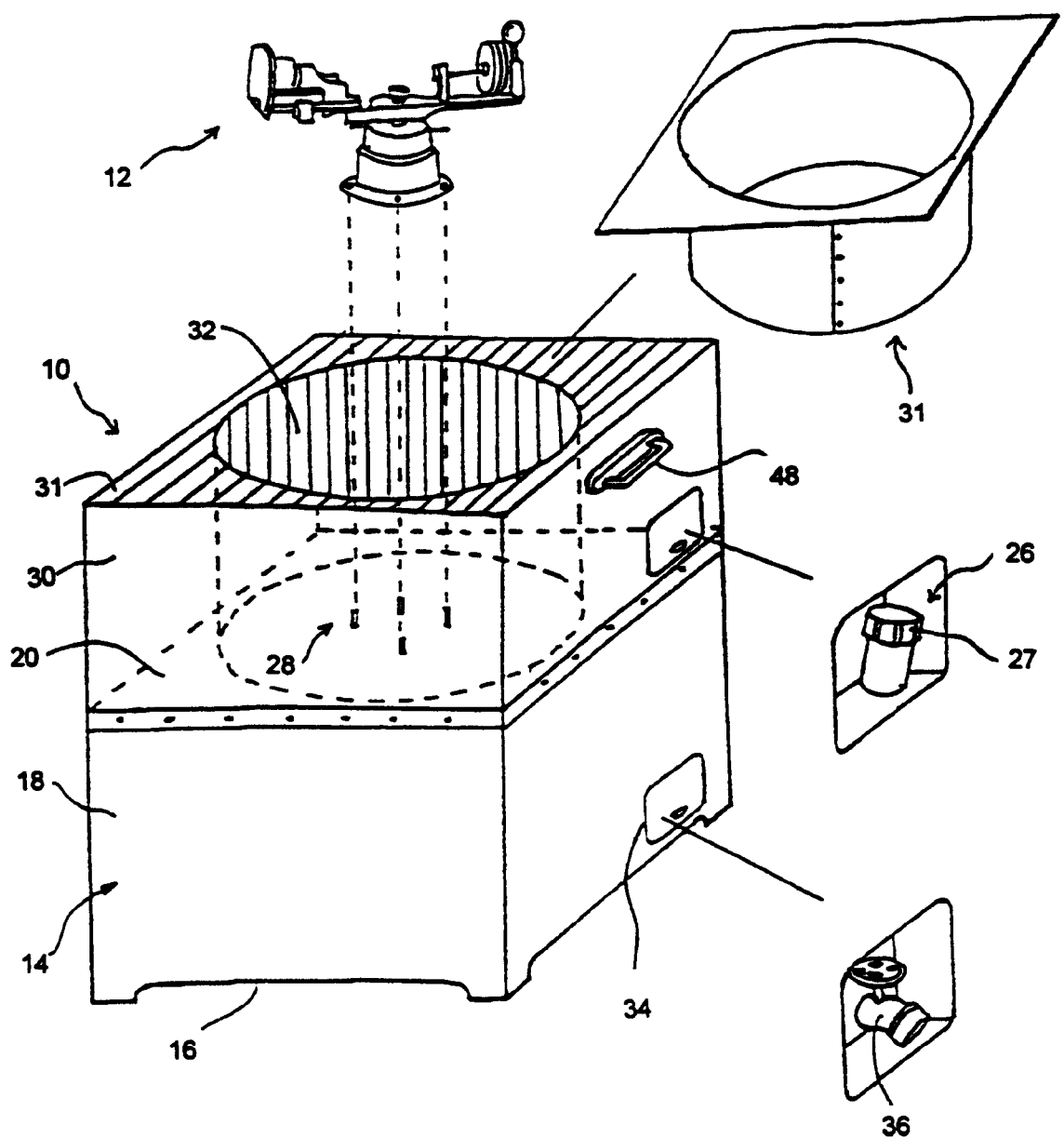
FIG. 1 is a perspective view of an embodiment of a centrifugal dental casting station with a rotating casting machine for a liquid type filler material according to the present invention.
Figure 2:
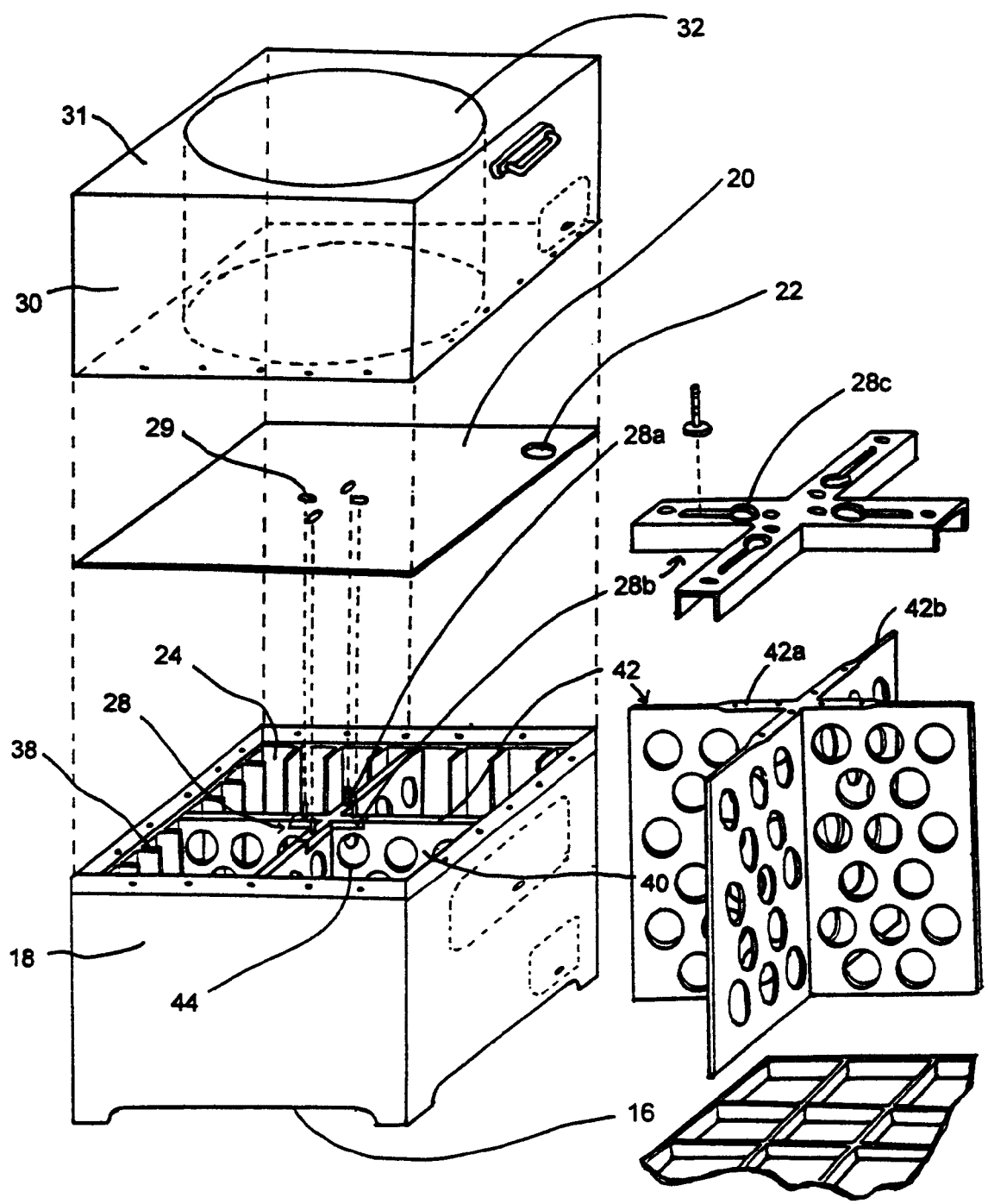
FIG. 2 is a perspective exploded view of the casting station of FIG. 1.
Figure 3:
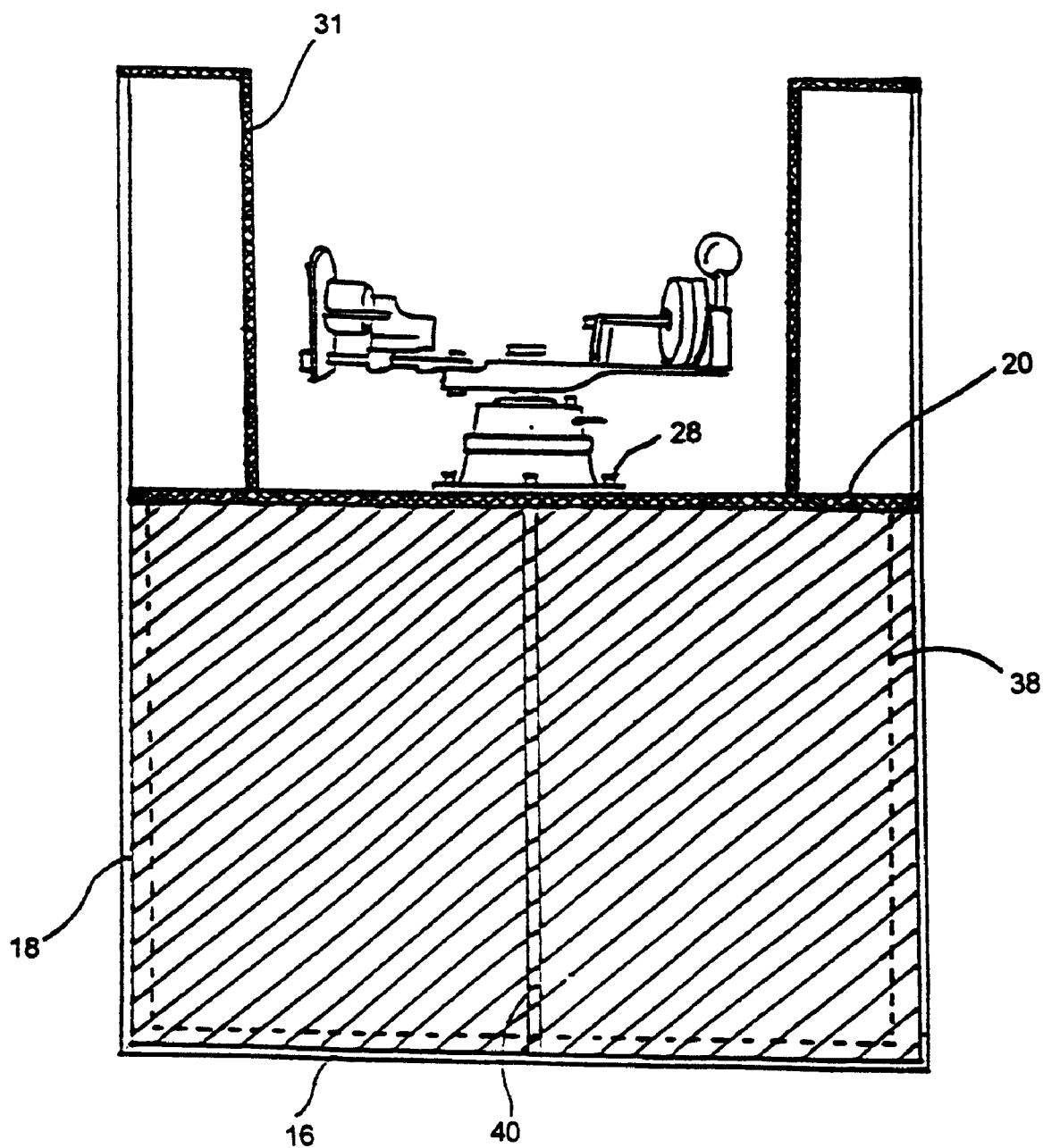
FIG. 3 is a cross-sectional view of the casting station with a casting machine in FIG. 1.

As shown in FIGS. 1, 2 and 3, the present invention provides a centrifugal dental casting station 10 for a rotating casting machine 12. The casting station 10 comprises a tank 14 for holding a filler material therein. The tank 14 comprises a base 16, side walls 18, a ceiling 20, and a first opening 22 for transferring the filler material into the tank 14 therethrough. The base 16, the side walls 18 and the ceiling 20 form a cavity 24. The cavity 24 can be filled with the filler material through the first opening 22. The first opening 22 may be formed through either the ceiling 20 or one of the side walls 18. Selectively, the first opening 22 may be formed through at least two of the side walls 18.

In an embodiment, a closing means 26 may be provided for closing the first opening 22. The closing means 26 may be selected from a cap 27, a valve or other closing devices. The closing means 26 covers the first opening 22 to enclose the filler material when the filler material is inserted into the cavity 24.

The centrifugal dental casting station 10 further comprises a support means 28 for supporting the rotating casting machine 12 thereon so that the casting station 10 can provide a substantially stable platform for operating the rotating casting machine 12 thereon. The support means 28 may be bolts 28a, screws or other connectable protrusions. The support means 28 may further comprise at least one bolt mount 28b fixedly attached to the upper edge of the cross-traversing partition. The bole mount 28b has a plurality of slide holes 28c therethrough. The bolts 28a are engaged through the slide holes 28c to the casting machine 12. The slide holes 28c enables a slidably adjustable bolt engagement depending upon the selected rotating casting machine 12.

The support means 28 provides attachment of the rotating casting machine 12 to the ceiling 20. To facilitate the attachment, the ceiling 20 may have holes 29 in correspondence to the support means 28. Specifically, the bolts 28a may be screwed through the slide holes 28c of the bolt mount 28b and through the holes 29 of the ceiling 20 to the casting machine 12, thereby realizing a stable attachment between the casting station 10 and the casting machine 12. The slide holes 28c enable a slidably adjustable bolt engagement so that the support means 28 adjustably secure the rotating casting machine 12 to the casting station 10 according to size of the rotating casting machine 12.

The centrifugal casting station 10 may further comprise a protective wall 30 mounted on the tank 14. The protective wall 30 is raised above the tank 14 and surrounds the support means 28. The protective wall 30 may comprise an inner protector 31 having an open space 32 so when the rotating casting machine 12 is installed onto the casting station 10, the inner protector 31 together with the protective wall 30 provides a substantial protection for the user. As shown in FIG. 3, preferably, the inner protector 31 and the ceiling 20 may be formed of aluminum to protect the casting station 10 and its operator from either the heat generated from the flame of a casting torch while the operator dissolves a casting metal on the rotating casting machine 12 or a possible fire which may occur during the casting operation.

In a preferred version, the tank 14 further comprises a second opening 34 for draining the filler material out of the tank 14. The tank 14 also comprises a valve 36 for regulating an outflow of the filler material through the second opening 34. For a better performance, the tank 14 further comprises baffles 38 attached to the base 16 and the side walls 18 inside the tank 14 to thereby allow a minimized thickness of the side walls 18 while maximizing the strength of the side walls 18.

In an embodiment, the tank 14 of the centrifugal casting station 10 further comprises a cross-traversing partition 40 having an upper edge 42 thereon. The cross-traversing partition 40 is attached to the base 16 and attached to the side walls 18 in the tank 14. In this construction, the cross-traversing partition 40 together with the upper edge 42 reliably supports the support means 28 such as bolts being engaged to the casting machine 12. Also, a plurality of through holes 44 are formed through the cross-traversing partition 40 to substantially decrease the overall weight of the casting station 10 and prevent eccentric convergence of the filler material when the level of the tank 14 is biased.

The tank 14 is substantially rectangular in shape. The tank 14 can be from about 20 inches to about 25 inches wide, from about 20 inches to about 25 inches long, and from about 18 inches to about 23 inches high. Further, the tank 14 can be shaped and sized to hold about 7,200 to about 15,000 cubic inches of the filler material when filled. Other sizes and shapes for the tank 14 are possible. The tank 14 can also be formed in a cylindrical shape.

A preferred size of the tank 14 is about 23 inches wide, 23 inches long and about 20 inches high, holding about 10,600 cubic inches of the filler material. The filler material can be one selected from water, sand, concrete bricks and other known filling materials.

Based on the weight and strength of the tank 14, different materials can be used for the tank 14 so that the casting station 10 can be light enough to make a product distribution through the dental supply system market and strong enough to support the vibration of the casting machine 12 while properly holding the filler material in the tank 14. For example, the tank 14 can be made from plastics or other fiber materials.

In case of plastics the possible thickness of the walls 18 for the tank 14 can be as thin as between about 0.12 inches and 0.25 inches depending upon the proper combination with the baffles 38 and the cross traversing partition 40. The thickness of each baffle 38 can be the same as that of each wall 18. The thicker part of the cross traversing partition 42a can be about 0.5 inches and the thinner part of the cross traversing partition 42b can be 0.25 inches. However, plastics are preferred material to meet the requirement of weight and toughness. Other materials can also be used.

Figure 4:
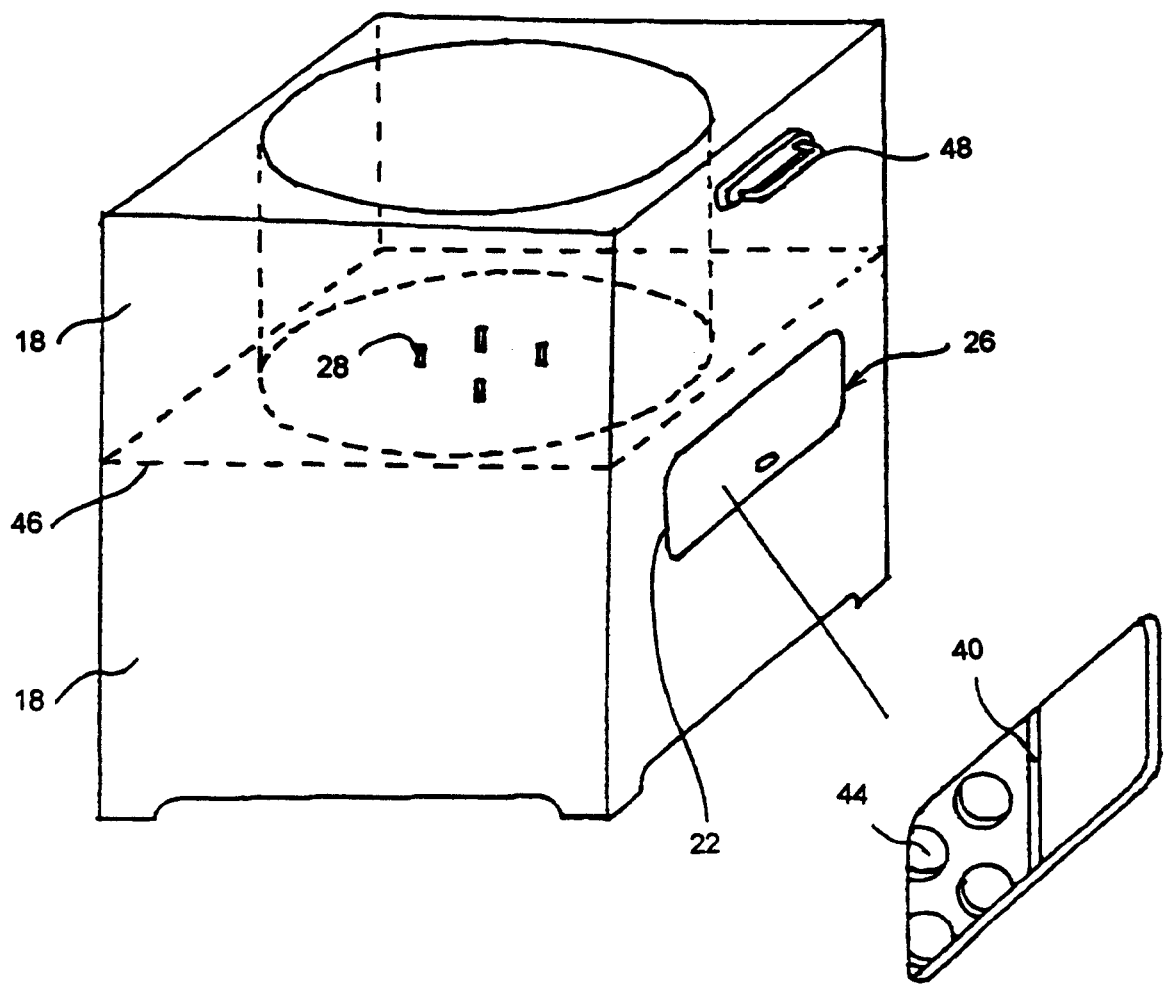
FIG. 4 is a perspective view of another embodiment of a centrifugal dental casting station for a solid type filler material according to the present invention.

As shown in FIG. 4, in another embodiment, the side walls 18 are upwardly extended as high as the upper part of the casting machine 12 in replacement of the protective walls 30 in FIG. 1. The side walls 18 have middle portions 46. The ceiling 20 is attached to about the middle portions 46 of the side walls 18. So the construction of the casting station 10 can be further simplified. In this structure, the inner protector 31 is fittingly mounted within the side walls 18 and over the ceiling 20 of the tank. Also, a pair of handle grips 48 can be selectively attached to the side walls 18 so that casting tools such as a casting torch and casting pincers can be hooked on the grips 48, thereby further facilitating the casting operation.

The advantages of the present invention are numerous. First, the present invention replaces the so far improvised casting stations for centrifugal dental casting machines being used in more than 80% dental labs in America and provides a standardized centrifugal dental casting station for thereby improving usability and work performance.

Second, the overall weight of the casting station is substantially decreased by thinnerizing the side walls while improving strength with the baffle and cross-traversing partition attachment to the side walls.

Third, the filler material in the tank can be easily adjusted in amount depending upon requirements in view of noise and vibration generated by the casting machine, thereby improving stability.

Fourth, the casting station according to the present invention, because of its lightweight and the adjustability of its weight, enables an easy installation and an easy transportation. Moreover, also because of its lightweight, when the filler material is removed, the centrifugal dental casting station along with the rotating casting machine can be easily leveled and its level can be easily adjusted when required in the future.

Although the present invention has been described in considerable detail with regard to the preferred versions thereof, other versions are possible. Therefore, the appended claims should not be limited to the descriptions of the preferred versions contained herein.

What is claimed is:

1. A centrifugal dental casting station for a rotating casting machine comprising:
   a) a tank having;
      (1) a base,
      (2) a plurality of side walls,
      (3) a ceiling,
      (4) a first opening,
      (5) a closing means for the first opening, wherein the base and the side walls form a cavity, wherein the cavity is covered by the ceiling, wherein the cavity can be filled with a filler material through the first opening, and wherein the filler material can be removed for an easy transportation of the centrifugal dental casting station,
      (6) a cross-traversing partition having an upper edge, wherein the cross-traversing partition is attached to the base and attached to the side walls in the tank; and
   b) a support means attached to the upper edge of the cross-traversing partition for supporting the rotating casting machine thereon, wherein the centrifugal dental casting station provides a substantially stable platform for operating the rotating casting machine thereon.

2. The casting station of claim 1 further comprising a protective wall mounted on the tank, wherein the protective wall is raised above the tank.

3. The casting station of claim 2 further comprising an inner protector.

4. The casting station of claim 3, wherein the support means comprises a plurality of bolts, and wherein the bolts provide a stable attachment of the rotating casting machine to the casting station.

5. The casting station of claim 4, wherein the support means further comprises a bolt mount fixedly attached to the upper edge of the cross-traversing partition and having one or more slide holes therethrough, wherein the bolts are engaged through the slide holes to the casting machine, and wherein the slide holes enable a slidably adjustable bolt engagement so that the support means adjustably secures the rotating casting machine to the casting station according to size of the rotating casting machine.

6. The casting station of claim 5, wherein a plurality of through holes are formed through the cross-traversing partition to substantially decrease weight of the casting machine while preventing eccentric convergence of the filler material when the level of the tank is biased.

7. The casting machine of claim 6, wherein the closing means is a cap covering the first opening to enclose the filler material when the filler material is inserted into the cavity.

8. The casting station of claim 7, wherein the tank further comprises a second opening for draining the filler material out of the tank.

9. The casting station of claim 8, wherein the tank further comprises a valve for regulating an outflow of the filler material through the second opening.

10. The casting station of claim 9, wherein the tank further comprises baffles attached to the base and the side walls inside the tank to thereby allow a minimized thickness while maximizing the strength of the side walls.

11. A centrifugal dental casting station for a rotating casting machine comprising:
    a) a tank having;
       (1) a base,
       (2) a plurality of side walls having middle portions,
       (3) a ceiling having attached to about the middle portions of the side walls,
       (4) a first opening,
       (5) a closing means for the first opening, wherein the base and the side walls form a cavity, wherein the cavity is covered by the ceiling, wherein the cavity can be filled with a filler material through the first opening, and wherein the filler material can be removed for an easy transportation of the centrifugal dental casting station,
       (6) a cross-traversing partition having an upper edge and attached to the base and the side walls in the tank; and
    b) a support means attached to the upper edge of the cross-traversing partition for supporting the rotating casting machine thereon, wherein the centrifugal dental casting station provides a substantially stable platform for operating the rotating casting machine thereon.

12. The casting station of claim 11 further comprising an inner protector.

13. The casting station of claim 12, wherein the support means comprises a plurality of bolts, and wherein the bolts provide attachment of the rotating casting machine to the casting station.

14. The casting station of claim 13, wherein the support means further comprises a bolt mount fixedly attached to the upper edge of the cross-traversing partition and having one or more slide holes therethrough, wherein the bolts are engaged through the slide holes to the casting machine, and wherein the slide holes enable a slidably adjustable bolt engagement so that the support means adjustably secures the rotating casting machine to the casting station according to size of the rotating casting machine.

15. The casting station of claim 14, wherein a plurality of through holes are formed through the cross-traversing partition to substantially decrease weight of the casting station while preventing eccentric convergence of the filler material when the level of the tank is biased.

16. The casting machine of claim 15, wherein the closing means is a cap covering the first opening to enclose the filler material when the filler material is inserted into the cavity.

17. The casting station of claim 16, wherein the tank further comprises baffles attached to the base and the side walls inside the tank to thereby allow a minimized thickness while maximizing the strength of the side walls.

* * * * *